(12) United States Patent
Stazzone et al.

(10) Patent No.: US 11,464,804 B1
(45) Date of Patent: Oct. 11, 2022

(54) INTRATHECAL MULTIFACTORIAL INFUSION OF HETEROGENEOUS AUTOLOGOUS CELL THERAPY

(71) Applicants: Enrico Stazzone, Carmel, IN (US); Madelyn Stazzone, Carmel, IN (US)

(72) Inventors: Enrico Stazzone, Carmel, IN (US); Madelyn Stazzone, Carmel, IN (US)

( * ) Notice: Subject to any disclaimer, the term of this patent is extended or adjusted under 35 U.S.C. 154(b) by 1003 days.

(21) Appl. No.: 16/188,649

(22) Filed: Nov. 13, 2018

Related U.S. Application Data

(60) Provisional application No. 62/586,534, filed on Nov. 15, 2017.

(51) Int. Cl.
| | |
|---|---|
| *A61K 35/28* | (2015.01) |
| *A61P 19/00* | (2006.01) |
| *A61L 27/38* | (2006.01) |
| *A61K 9/00* | (2006.01) |
| *A61B 17/00* | (2006.01) |
| *A61B 17/56* | (2006.01) |
| *A61F 2/46* | (2006.01) |
| *A61K 35/12* | (2015.01) |
| *A61B 90/00* | (2016.01) |

(52) U.S. Cl.
CPC ............. *A61K 35/28* (2013.01); *A61B 17/00* (2013.01); *A61B 17/56* (2013.01); *A61F 2/46* (2013.01); *A61K 9/0019* (2013.01); *A61L 27/3834* (2013.01); *A61P 19/00* (2018.01); *A61B 2017/564* (2013.01); *A61B 2090/374* (2016.02); *A61K 2035/124* (2013.01); *A61M 2202/10* (2013.01)

(58) Field of Classification Search
CPC ............ A61K 35/28; A61K 9/0019; A61K 2035/124; A61P 19/00; A61B 17/00; A61B 17/56; A61B 2090/374; A61B 2017/564; A61F 2/46; A61L 27/3834; A61M 2202/10
USPC ........................................................ 604/522
See application file for complete search history.

(56) References Cited

U.S. PATENT DOCUMENTS

| | | |
|---|---|---|
| 6,653,134 B2 | 11/2003 | Prockop |
| 7,129,034 B2 | 10/2006 | Yu |
| 7,364,900 B2 | 4/2008 | Black |
| 7,605,128 B2 | 10/2009 | Greenberg |
| 8,017,112 B2 | 9/2011 | Li |
| 8,900,574 B2 | 12/2014 | Kadouri |
| 8,940,293 B2 | 1/2015 | Li |
| 2003/0185803 A1 * | 10/2003 | Kadiyala ............ A61L 27/3616 435/372 |
| 2008/0019970 A1 * | 1/2008 | Gorman ............ A61K 31/4164 514/401 |
| 2009/0162327 A1 | 6/2009 | Li |
| 2012/0276068 A1 | 11/2012 | Sabaawy |

FOREIGN PATENT DOCUMENTS

WO      WO 97/40137      * 10/1997

* cited by examiner

*Primary Examiner* — Yih-Horng Shiao
(74) *Attorney, Agent, or Firm* — CreatiVenture Law, LLC; Kevin C. Staed; Dennis J M Donahue, III (57) ABSTRACT

A method of treating spinal cord injuries in a patient using sagittal MR images of the spinal cord injury to guide the extent of exposure of the neuro/orthopedic surgeon during a posterior spinal fusion for the purpose of autologous stem cell therapy in the setting of spinal injury; the method using large volumes of the patient's bone marrow aspirated to yield a large quantity of heterogeneous autologous stem cell concentrate containing cellular and subcellular fractions, in addition to soluble protein factors (defined as heterogeneous concentrate) exhibiting regenerative potential which is then applied directly over the spinal cord (under the dura/arachnoid) in the areas affected.

13 Claims, 3 Drawing Sheets

INTRATHECAL MULTIFACTORIAL INFUSION OF HETEROGENEOUS AUTOLOGOUS CELL THERAPY

CROSS-REFERENCE TO RELATED APPLICATIONS

This application claims the benefit of provisional patent application 62/586,534 filed Nov. 15, 2017, which is hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

This invention relates to the utilization of autologous stem cell therapy in spinal cord injury utilizing MRI findings to guide the extent and volume of the infused material which is directly applied to the spinal cord via infusion ("bathing" technique) after the surgeon obtains exposure for posterior fusion.

Related Art

The use of intrathecal administration of autologous cell therapy has been documented in acute, subacute and chronic spinal cord injury (SCI) with mixed results. The approaches have been variable with no one standardized technique considered optimal to date. Stem cells, either culture expanded or those derived from bone marrow using a point-of-care concentration device, have been transplanted by IV injection, intralesional route, intrathecal injection or injection into the spinal artery. Approaches have also included a variety of volumes, cell types and adjunct techniques such as the use of bio-absorbable scaffolding and stem cell modification. In addition, in vitro and in vivo preclinical results have not correlated with clinical outcomes. In vitro evidence suggests that cell therapy may provide healing to the injured spinal cord by generating neural or myelin producing cells. In a review of large animal studies, Gabel et al. found that animals treated with stem cell therapy showed improvement in functional outcomes, illustrating that there is potential therapeutic benefit. Although promising, to date no one technique has proven ground breaking and the need for improvement and standardization has been discussed by leaders in the field.

Patients with severe cervical injuries and cord compression fail to recover significant function years after injury, even in the best of centers with state-of-the-art physical therapy techniques. The pathophysiology is well documented. Injury to the spinal cord results in a transient production of chemokines and cytokines which produce a secondary inflammatory cascade leading to apoptosis, necrosis, and glial scar formation.

In the third world, cervical spinal cord injuries are certainly devastating, especially for the poor with little access to rehabilitation therapy. In the United States of America, standard treatment of a patient with SCI involves prompt assessment utilizing the American Spinal Injury (ASIA) impairment scale followed by stabilization. Imaging is then performed (cervical spine radiographs, CT, MRI) followed by halo traction placement, unless contraindicated (in the setting of skull fracture and vertebral artery dissection), followed by surgical decompression and fusion (anterior or posterior). Although in the past, high dose IV methylprednisolone administration was considered standard of care in acute treatment, that is no longer the case and it is now considered optional. McMillan, et. al's 2016 observational study in R. Adams Cowley Shock Trauma Center at the University of Maryland Medical Center advises against methylprednisolone administration as the benefits do not seem to outweigh the risks (infection). Magnetic resonance (MR) imaging is helpful in defining the extent of the damage of the spinal cord, especially T2 weighted images (T2WI) in the sagittal plane. The classic SCI presents as a spindle-shaped intramedullary area of high signal on T2WI with central hemorrhage and peripheral edema. Complete SCI is defined as no preservation of voluntary motor function or sensation below the lesion, whereas incomplete SCI exhibits varied motor and sensory loss below the level of the lesion due to sparing of some neural tracts. The ASIA scale at initial evaluation is considered to be the most relevant prognosticator of functional recovery, with ASIA A patients having the poorest prognosis and ASIA E having the best. However, expedited care is also felt to play a role in outcome. The phases of injury are:

Immediate—within 2 hours of injury
Acute—>2 hours-48 hours
Subacute—>2 days-≤14 days
Intermediate—≤6 months
Chronic—>6 months While prompt treatment in the acute phase of SCI is recommended, underdeveloped countries report a high rate of neglected assessment of traumatic SCI which can result in increased mortality and severity of complications, in addition to dire prognosis for functional recovery. An observational study by Bourassa-Moreaus, et al., in 2016 looked at 20 patients with complete cervical SCI (ASIA A) and found that 64% of those who underwent decompression and stabilization within 24 hours after injury showed improvement as opposed to 0% in those who underwent corrective surgery after 24 hours.

As mentioned above, post-traumatic inflammatory reactions play a critical role in the secondary injury processes that occur after SCI. Mechanical compression of the spinal cord can lead to ischemic injury and neuronal death that may be exacerbated by tissue reperfusion subsequent to decompression and stabilization. Neurons continue to die for several hours and days after injury. The best approach to limiting catastrophic tissue damage following SCI has yet to be elucidated. New discoveries in this aspect of neuroscience could therefore fulfill a great unmet clinical need.

Biochemical regulatory mechanisms have been described by which microglial cell activation promotes oligodendrocyte death. Apoptosis resulting from microglia-mediated production of toxic cytokines such as IL-1 beta and TNF-alpha has been demonstrated both in vitro and in pre-clinical animal studies following mechanical injury. Downstream regulators induce a catabolic cascade characterized by lipid peroxidation and induction of genes regulating the synthesis and secretion of proteases with potential to destroy basement membrane, collagen- and proteoglycan-rich ECM, and myelin—the fatty insulation that normally protects most nerves in the brain and spinal cord. Progressive neurodegeneration has devastating consequences in patients with spinal cord injuries.

Recent pharmacologic approaches (corticosteroid) to reduce acute and chronic inflammation secondary to SCI are considered ineffective and associated with significant side effects. The development of novel biologic approaches potentially leading to tissue repair and regeneration holds great promise in the field of SCI because these treatment options are reported to deliver a natural complement of trophic factors and anti-inflammatory proteins capable of restoring tissue structure and function, in addition to cells displaying regenerative potential. However, positive experimental results in animals have failed to show direct translation to humans. Stem cell therapy and/or administration of heterogeneous fractions of bone marrow and whole blood containing trophic factors are generally recognized as safe and continue to demonstrate positive clinical outcomes in a variety to degenerative diseases and soft tissue injury.

Bone marrow is a complex tissue comprising several cell subpopulations, including hematopoietic stem cells (HSC), progenitor cells, leukocytes, and mesenchymal stromal stem cells (MSC). This heterogeneous population of regenerative cells is recognized to express multi-lineage differentiation potential to several musculoskeletal tissues, including those of the osteogenic (bone), chondrogenic (cartilage), and adipogenic (adipose) lineage. Additionally, platelets present within bone marrow or whole blood provide trophic factors critical to the recruitment and expansion of MSC and may offer protection from apoptotic pathways. In addition to MSC, bone marrow contains a larger population of CD34+ cells demonstrated to play a role in revascularization after tissue injury, either directly through repopulation or indirectly via the secretion of trophic factors. Given the autologous nature of bone marrow aspirate and platelet-rich plasma, potential side effects or complications associated with their administration is theoretically reduced. With respect to regeneration of neural tissue, Kaka et al (2012) reported the ability to transdifferentiate oligodendrocytes in vitro from bone marrow derived stromal cells with sequential exposure to platelet derived growth factors (PDGF-AA and FGF-2) and triiodothyronine. Past studies have further shown in vivo administration of bone marrow stem cell (BMSC} to improve oligodendrogenesis in rodents after stroke injury. PDGF is recognized to be both neurotrophic and neuroprotective, supporting neuronal differentiation in vitro. Vascular endothelial growth factor (VEGF) has demonstrated similar activity.

Mechanical concentration of bone marrow to largely remove unwanted red blood cells has recently led to the identification of proteins with potent anti-inflammatory activity, providing immediate pain relief upon intra-articular and/or soft tissue administration. Both interleukin 1 receptor antagonist and TNF-alpha soluble receptor actively bind to its respective cytokine target to neutralize receptor binding. Each of these proteins are reported to be present at higher concentration in bone marrow as opposed to whole blood after centrifugation of these fluids. The role which these factors play in regulating tissue injury and possible recovery following SCI remains poorly studied. A less studied component of bone marrow but present in high numbers relative to nucleated cells are microvesicles or exosomes which are described to carry a variety of cargo proteins (growth and trophic factors), DNA and RNA sequences regulating a multitude of activities, including but not limited to positive and negative differentiation factors and anti-inflammatory pathways. This fraction is lighter than platelets and unknowingly delivered as part of the platelet poor plasma fraction once whole blood or bone marrow is subjected to volumetric concentration to remove red blood cells. Future investigations must explore the potential clinical utility of bone marrow derived exosomes to promote functional recovery after traumatic SCI.

The following exampled show fast, marked improvement in the functional and neurological parameters after documented complete/near complete cervical SCI in response to localized delivery of an autologous cellular therapy derived from bone marrow aspirate in human subjects. According to Chhabra et al., " . . . because of the involvement of multiple cell types and the complexity of SCI, it is becoming increasingly clear that a single approach [as used in their studies] may not by successful in achieving SCI repair. A multifactorial approach involving inhibition of secondary cascade events, molecular therapy, cell transplantation, bioactive scaffolding matrix, growth factor supplementation and scar removal is required to address this situation." The technique method described within, achieved repeatable results in two consecutive patients using a multifactorial approach. Moreover, the results were obtained quickly and despite a marked delay in decompression and cervical fusion, very limited physical therapy supplementation, and inhibitory factors that do not face SCI patients in the US.

SUMMARY OF THE INVENTION

This technique involves the use of sagittal MR images of the spinal cord to guide the extent of exposure of the neuro/orthopedic surgeon during a posterior spinal fusion for the purpose of autologous stem cell therapy in the setting of spinal injury. Furthermore, large volumes of bone marrow (about 240cc or more) are aspirated to yield a large quantity of heterogeneous autologous stem cell concentrate containing cellular and subcellular fractions, in addition to soluble protein factors (defined as heterogeneous concentrate) exhibiting regenerative potential which is then applied directly over the spinal cord (under the dura/arachnoid) in the areas affected, as guided by MRI findings. The technique necessitates a posterior fusion approach since the spinal cord must be exposed for direct stem cell infusion.

The novelty of this technique is that a posterior approach is used whereby large volumes of bone marrow are aspirated, approximately 240cc to yield a large quantity of bone marrow concentrate, e.g., approximately 20cc. The bone marrow aspirate undergoes a centrifugation process after yielding three distinct layers: the deeper red blood cell layer, the bone marrow concentrates (buffy coat containing some platelets) and the superficial plasma layer containing an abundance of platelets, exosomes and soluble protein factors. Bone marrow concentrate (BMC) is isolated and utilized for stem cell therapy. In both cases described below, 10cc of BMC was used to "bathe" the injured spinal cord from just cephalad to the superior aspect of the lesion to just caudal to the inferior aspect of the lesion. After the dura is closed by the surgeon, another 10cc of BMC is soaked to a piece of GELFOAM sterile sponge and placed on top of the sutured dura. The concentrated, superficial plasma (approximately 30cc) is then split evenly and applied over the GELFOAM and muscle layer after the muscle is sutured.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

BRIEF DESCRIPTION OF THE DRAWINGS

DETAILED DESCRIPTION OF THE PREFERRED EMBODIMENTS

The following description of the preferred embodiment(s) is merely exemplary in nature and is in no way intended to limit the invention, its application, or uses.

Figure 1:
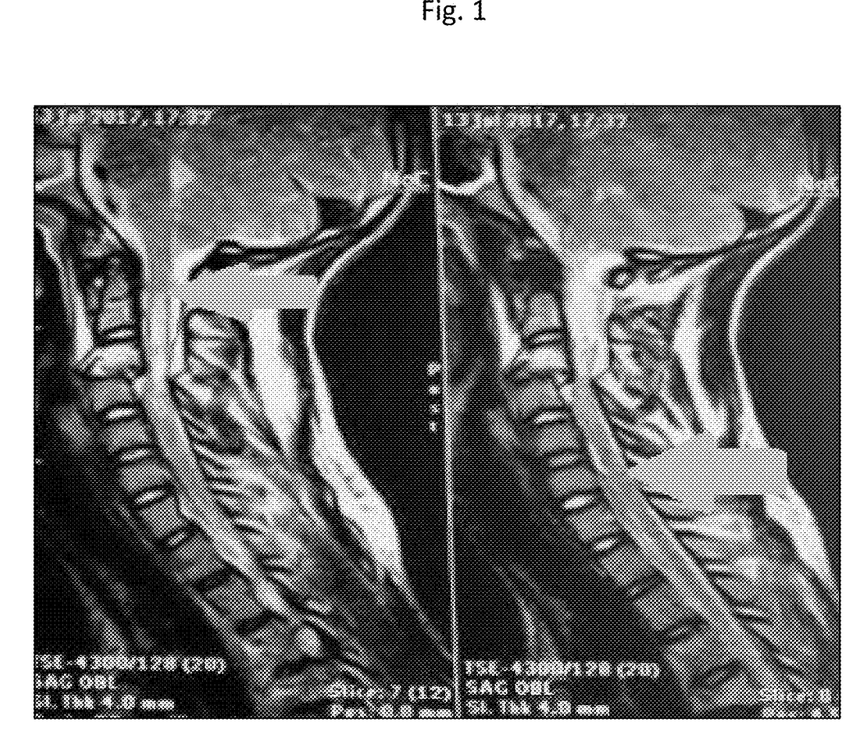
FIG. 1 shows the contiguous Sagittal T2W MR Images of 15-year-old boy after motorcycle accident show C3-4 fracture subluxation with abnormal high central spinal cord signal delineated by yellow arrows extending from C2-C6

Example 1—A technique described herein was developed as an attempt to salvage some function in a 15-year-old boy admitted with a severe cervical injury to the Hospital Infantil Dr. Arturo Grullón, a public children's Hospital in Santiago, Dominican Republic. He had sustained a motorcycle accident. Imaging studies (plain films and MRI) showed a burst fracture of C3 with posterior subluxation and disrupted C3-4 disc resulting in cord compression and hemorrhage. Sagittal T2WI showed abnormal high intramedullary spinal cord signal with peripheral edema extending from the level of C2-C6. Initial physical exam showed quadriplegia, that is, no sensory or motor function below the level of injury in the neck (ASIA scale A). He also had a fractured tibia which was treated with external fixation and casting. The patient received high dose methylprednisolone, initiated upon arrival to the hospital and tapered over 4 days as per the local surgeons' protocol. Because of limited insurance coverage, the implants required for surgery were not approved for several days and his surgery further delayed secondary to dilapidated operating room conditions and limited operating room access secondary to ongoing construction. A halo traction device was placed 8 days after surgery. The insurance company dictated the surgical approach, approving implants for a posterior fusion, not anterior. In the end, surgery was not performed until 10 days after injury. He received a second regimen of high dose steroids for 4 days peri-operatively (same as on arrival) again, as per the protocol of the local surgeons. The patient received decompression with infusion of BMC via the claimed method and posterior fusion. During the surgery, the covering of one of the walls of the OR collapsed, exposing mold and mildew and contaminating some of the instruments on one of the OR tables, which were then not used in surgery. Because of this, the patient was treated with antifungal antibiotics for several days. Within 17 hours after surgery, he could shrug both shoulders and slightly move his right thigh. Within 2 days he could contract his left thigh. At 4 days after surgery, he could lift his left thigh off the bed and plantar flex his left foot. He continued to have improvement in sensation and motor ability over the next few months. At 3 months after surgery, he could feed himself, lift legs against gravity, stand and initiate a step with his left foot. Unfortunately, his right knee has limited mobility as a result of his tibial fracture, but he could move both legs and feet, left better than right.

Figure 2:
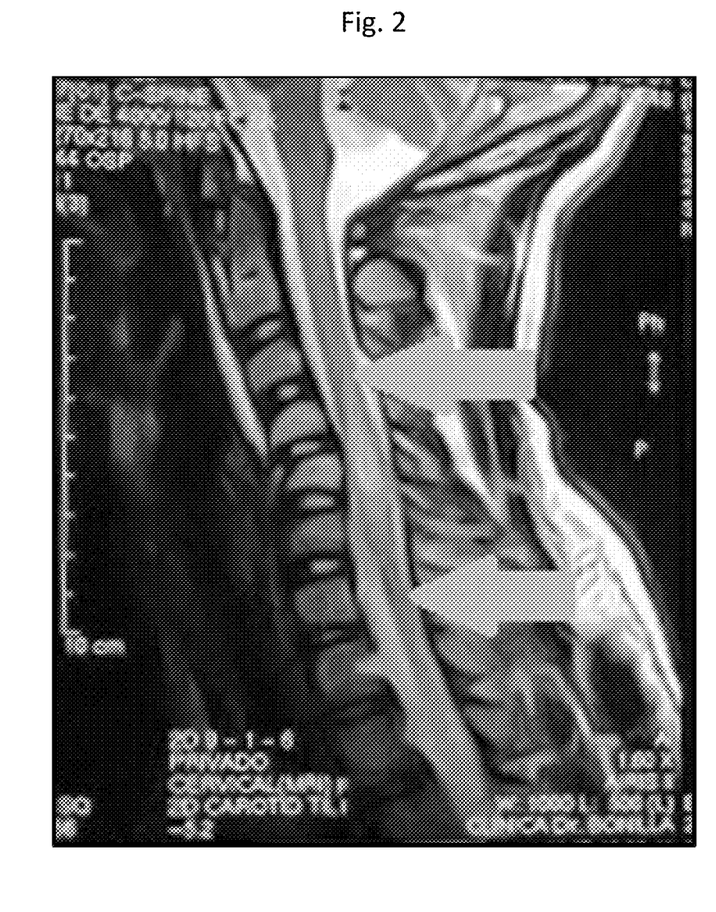
FIG. 2 shows T2W MR Images of 17-year-old boy after motorcycle accident show C4-5 fracture subluxation with classic spindle-shaped spinal cord central hemorrhage and peripheral edema delineated by yellow arrows extending from C3/4-C7
Figure 3:
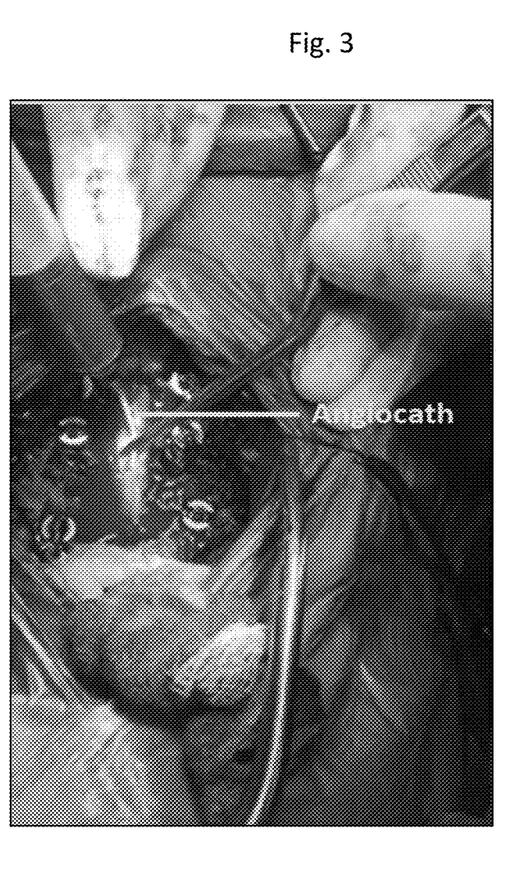
FIG. 3 shows the intra-operative image of the cervical surgical bed during a posterior fusion shows infusion of BMC under the dura.

Example 2—The same technique was utilized in a 17-year-old boy admitted to the same facility after a motorcycle accident with fractures of C4 and C5 with anterior subluxation of C4 on C5 and spinal cord compression (ASIA scale B). Pre-operatively he could slightly elevate his right scapula and minimally abduct his right shoulder. He had sensory loss below T4. Sagittal T2WI showed the classic spindle shaped intramedullary spinal cord lesion with central hemorrhage and peripheral edema extending from the level of the C3-4 disc space to the C7 vertebral body. This patient also received high dose methylprednisolone for 4 days as per their hospital protocol, initiated upon arrival to the hospital. He was not placed in halo traction, a decision made by the local surgeons. He was also impoverished, with less coverage than the first patient and the operating room situation had worsened such that when posterior spinal fusion and decompression surgery was finally performed 25 days after injury, he had to be transferred to another hospital for the procedure. Again, the insurance company dictated the approach (posterior). He also received a second regimen of high dose steroids for 4 days peri-operatively. This patient also received decompression with infusion of BMC and posterior fusion. Upon awaking from surgery, he could move his left elbow slightly. Within 2 days he could abduct both arms and had recovered sensation to the tip of his toes and fingers. At 8 days post-op, he could abduct both arms well, right more than left. At 12 days post-surgery the patient had started to have voluntary movement in his right lower extremity.

In both surgeries, the described technique was an attempt to salvage some function and regain some normalcy of quality of life. Both patients exhibited remarkable improvement shortly after surgery, despite having severe cervical injuries and delayed treatment. Patients with ASIA A cervical injuries historically have a 1-3% chance of regaining any function but in the setting of delayed surgery (like the first patient) the chances go down to 0%. Patients with ASIA B cervical injuries historically have a 33% chance of regaining some function although the data is highly variable. However, given the 25-day delay from injury to surgery in the second patient, the chances of him regaining mobility are considered slim. It should be also noted that neither of these young boys have access to advanced technique physical therapy personnel or any type of technology that would expedite function, movement, and sensory. Despite the lack of resources, technology, and access to post-operative medical care, both patients' collective improvement would be considered nothing less than breakthrough and remarkable.

In various embodiments, various commercially available centrifugation systems, fenestrated bone marrow aspiration needles, flexible catheters or something similar, hemostatic hydrogels or something similar, could be used to recreate parts of this method. One skilled in the art could individually select parts of this method to differentiate a new proprietary method for infusing bone marrow concentrate intrathecally.

First, we will describe the differentiating surgical technique, the bone marrow aspiration, and then the bone marrow concentration process.

Surgical Technique:

Step 1: The extent of the spinal cord damage is identified on sagittal T2W MR images. The extent of the spinal therapy is then defined from just cephalad to the superior aspect of abnormal signal to just caudal to the inferior aspect of spinal cord signal.

Step 2: This step of the technique method necessitates a posterior fusion approach to the cervical spine for spinal cord injury. The posterior cervical approach chosen by the local surgeons to decompress the spinal cord involved removing the posterior aspects of the bone covering the spinal cord and incising of the skin, muscle, dura and arachnoid to gain access to the cervical aspect of the spinal cord. This allowed for injection of the BMC to all injured areas. In contrast, an anterior cervical spine approach would not have allowed access to the spinal cord because it does not involve incising the meninges (dura/arachnoid) and exposing the spinal cord. If an anterior approach were to be used, adequate injection of cell therapy underneath the dura mater, would not be feasible.

Step 3: This step of the technique method entails guiding the surgeon's midline dural incision based on MRI findings. The incision length will vary depending on the number of injured levels and extent of cord damage. The guideline was to incise half the length of the damaged cord length, centering it on the lesion. In both cases, the incision did not extend past 4 cm in longitudinal length. A 4 cm incision of the dura mater adequately provides visualization of the spinal cord and access to the circulating spinal fluid matter. Additionally, a smaller incision ensures the outer dura encloses the injected therapy keeping the cell/host contact intimate.

Step 4: This step of the technique method describes the injection of BMC containing a heterogeneous mix of healing factors. A novel use of a flexible tip angiocath is inserted underneath the dura layers and the bone marrow injection is slowly injected or "bathed" of the injured cord. The angiocath tip is inserted further underneath the dura and the "bathing" injection is repeated to all cord levels showing injury via MRI. The "bathing" and insertion should be done sequentially, making sure only to inject ½ to 1 ml of concentrate for every 1 cm of insertion. Injection pressure should be slow and monitored. Sequential steps should be slow, deliberate, and patient so as not to increase the spinal cord pressure with fluid. These sequential steps should be repeated to the most superior and inferior aspects of the injured cord from the level of primary injury. A total of 10 ml of heterogeneous concentrate (half of the total injection) should be injected underneath the dura mater.

Step 5: This step of the technique method is a novel use of surgical GELFOAM sterile sponge as a cell delivery vehicle. Following closure of the dura by the surgeon, the remaining 10 ml of BMC is soaked to a resorbable piece of surgical GELFOAM and placed on top of the sutured dura mater. GELFOAM Sterile Sponge is a medical device intended for application to bleeding surfaces as a hemostatic. It is a water-insoluble, off-white, nonelastic, porous, pliable product prepared from purified pork skin gelatin granules and water. It may be cut without fraying and is able to absorb and hold within its interstices many times its weight of blood and other fluids. It is a commonly used material for surgical clotting and hemostasis. Although it's mechanism of action is not well understood, it is believed to result in the local production of thrombin, initiating the clotting cascade. Thrombin converts fibrinogen to fibrin, and can activate platelets to bind to fibrin, thus initiating clotting. Moreover, GELFOAM is primarily made of porcine and a resorbable polymer. Porcine and resorbable polymers have been long established with respects to tissue regeneration and cell delivery vehicles. Although certain polymers and xenograft tissues have been known to elicit unwanted inflammatory responses, GELFOAM has long been used around the spinal cord for spinal cord dura leaks or hemostasis and is considered safe. It is well known and established that the first stages of any tissue to regenerate in the body is the formation of a clot. Once a clot is formed, the body recognizes this critical step as the beginning cascade to initiate repair, cellular recruitment, and site repair of injured tissue. In the case of spinal cord injuries, with the presence of scar tissue and cell death, this normal healing cascade could not begin naturally. The infused gel foam provides the ideal, safe, material to initiate repair of the incised dura mater by clot formation. It also, stimulates the platelets from the cell infusion injection to activate adhesion proteins and growth factors to further contribute to clot formation. These represent the first stages of tissue regeneration and wound healing to the otherwise dormant injured spinal cord. Lastly, the GELFOAM provides the ideal cell delivery vehicle to time release progenitor cells, trophic factors and proteins due to its resorption characteristics.

Step 6: This step of the technique method describes delivery of the platelet-rich plasma. Prior to closing of the muscle/fascia layer, the remaining volume of concentrated platelet-rich plasma volume (30cc) is divided evenly and half (15cc) is applied over the GELFOAM and the surrounding wound bed. The muscle fascia complex is then closed by the surgeon and the remaining 15cc of platelet-rich plasma is applied over it. Administering of platelets encourages, cell attraction, proliferation, and angiogenesis. All of which are vital and necessary to regenerating tissue, yet not known in the application of spinal cord injury.

The bone marrow aspiration technique used to prepare the BMC exhibits surprisingly rapid regenerative potential when applied to the injured spinal cord as described below. One of the most important points to this entire process is the amount of bone marrow aspirated. Many established tissue regeneration models understand the importance of taking high volumes of bone marrow aspirate. Yet, in the known spinal cord injury studies, only small volumes of bone marrow are commonly aspirated. The maximum volume that is known to be feasible in the clinical setting is aspirated, and known bone marrow aspiration techniques were utilized to ensure highest yields of progenitor cells and platelets/ml possible before centrifugation. All of this is described below:

Bone Marrow Aspiration:

Step 1: Standard heparinization of fenestrated bone marrow aspiration needles and 10 ml syringes.

Step 2: 120 ml of bone marrow was aspirated from each posterior iliac crest, yielding a total of 240 ml. Bone marrow was aspirated in 10 ml syringe aliquots according to established techniques. Sequential needle advancements were undertaken according to established aspiration techniques, as well as, changing the needle trajectory. These steps were taken until a total of 120 ml of bone marrow aspirate was taken from one posterior iliac crest. The same process was undertaken for the contralateral iliac crest until a total of 240 ml of bone marrow was aspirated. In contrast, known spinal cord injury studies only aspirate 60 ml of bone marrow and do not adhere to meticulous bone marrow aspiration technique. The delivery of as many cells as possible is critical to tissue regeneration, particularly neural tissue.

Step 3: Centrifugation (described below)

Step 4: A volume reduction factor of approximately 10-fold was used for centrifugation. A total of 20 ml of bone marrow concentrate was yielded from the starting volume of 240 ml.

Step 5: Bone marrow concentrate was delivered back to the sterile field and aspirated into 10 ml syringes. A flexible angiocath tip was attached via a luer lock fitting to the distal end of the syringe and ready for delivery.

Bone Marrow Concentration Via Centrifugation:

Bone marrow was processed using a hospital blood bank laboratory cell separation centrifuge. Bone marrow was divided equally into the 4 processing bags and placed into the swing bucket rotors. Bone marrow was processed for approximately 14 minutes at 3000 rpm. Following centrifugation, a heterogeneous concentrate containing the superficial plasma layer and BMC (buffy coat) layers were removed from each processed bag leaving only the heavier red blood cells. The superficial plasma and BMC syringes were each aspirated into different syringes.

The novelty of this method is in its inherent empirical wisdom of understanding of how tissue regeneration works, and the combination technique involved.

Bone marrow, as opposed to whole blood, is the only autologous source housing the necessary progenitor cells, exosomes, anti-inflammatory proteins, and growth factors that in synergy can potentially restore neurological function, but must be taken in large aspiration volumes. Various small sample studies have reported that bone marrow concentrate cell therapy for spinal cord injuries shows no efficacy. However, these studies inherently missed that large volumes of marrow are needed for tissue regeneration, an important principle. For example, in 2016 Chhabra et al. looked at intralesional injection and intrathecal injection of stem cells after thoracic spinal cord injury and found no benefit. However, the volume of bone marrow aspirated was 60cc and the volume of BMC injected was 1.8cc. This technique determines bone marrow aspiration volumes by the extent of damage along the spinal cord as evidence by MRI findings. In both cases the spinal cord lesion spanned along 5 cervical levels. In this technique, the volume of marrow aspirated from the patient was 240cc and the BMC administered to each was 20cc total, with half of the volume (10cc) administered intrathecally (bathing of cord technique superior and inferior to injury) across 5 levels of cord abnormality and half (10 cc) administered on top of the dura to hydrate a cell delivery carrier vehicle. The embodiment of cell therapy literature demonstrates therapeutic benefits can only be obtained from large autologous volumes to obtain an optimal therapeutic treatment volume per ml. Surprisingly, the published literature directed at spinal cord injury reports minimal volumes of bone marrow aspirate harvested for therapeutic application. The volume used for delivery is determined by how much is aspirated and yield of a concentrate as well as by the extent of the cord damage. In both cases, a total of 20cc of concentrate was delivered to cover the length of 5 cervical levels.

The technique utilizes proven aspiration technique to optimize the number of cells/ml aspirated to be concentrated to yield a large volume and or number of cells required to adequately cover the extent of cord damage seen on the MRI. It has been shown that aspiration in the iliac crest, small sized syringes, and aspiration needle movement are necessary in order increase the number of cells yielded in the aspiration. This technique combines all three. Therefore, bone marrow was aspirated in small volume syringes, while utilizing anatomical needle movement, in the iliac crest, producing a large total volume determined by the extent of the cord damaged.

Other tissue regeneration models have demonstrated and established the importance of not only direct injection to the primary injury site, but also sequentially injecting beyond the primary site. This fundamental principle underscores the importance of surrounding vasculature and the interdependence of an entire damaged area, not just the injured bony levels. This principle is not utilized in other clinical models injecting into the spinal cord. These other models only injected directly to the site of bony injury or up to a level above and a level below, missing the fact that the spinal cord injury can extend further cephalad and further caudal to the bony injury. This is a crucial concept since electrical impulses travel cephalo-caudal and if the cephalad portion of the spinal cord damage is not treated, impulses will be halted at that level and recovery will not be possible. Therefore, using the spinal cord abnormality as a gauge of damage, rather than the bony abnormality, makes more sense. Some studies injected patients with cervical and thoracic SCI's in the lumbar region (via LP), thus depending on the circulating spinal fluid to carry stem cells to the damaged areas. The present method is not a localized injection into the cord, an intrathecal lumbar puncture injection or superficial placement on top of the dura like other similar studies. The present method requires incision of the dura over the injured level to have access to the entire injured spinal cord segments. The cell therapy "bathes" the affected areas of the spinal cord and the dura over the entire area of damage levels as verified by MRI. In doing so, the entire damaged area benefits from direct cell/tissue contact necessary for tissue regeneration. Furthermore, it is surmised that the bathing/infusion technique repairs any fibrous scar tissue present underneath the dura due to injury that a localized or superficial dura injection would not address. It should be noted that in the second case described, we saw pulsation activity in the newly "bathed" spinal cord. This may be secondary to dislodging of fibrous scarring material and progenitor cells quickly recognizing cell/host response resulting in prompt transmission of impulses. The BMC "bathing" infusion that spans the length of the spinal cord lesion in this technique is believed to disrupt fibrous scar tissue present intrathecally. In addition, progenitor cells are delivered directly to the area of spinal cord damage ensuring cell to host contact as opposed to centering the delivery at the site of bony damage or delivering via lumbar puncture (far away from the spinal cord lesion) as in prior reports.

The cell therapy is treated by novel use of a flexible angiocath delivery device. This provides tremendous benefits within a razor thin space, allowing cells to be delivered in a controlled fashion over the entire injured areas of the spinal cord, underneath the protective layer of the dura, in an enclosed space, and ensuring the therapeutic progenitor cells are free from other competing cells circulating in the injured environment. This novel use enables the physician to insert the flexible, needleless tip underneath the dura of the spinal cord without incising the entire spinal cord of damaged area. Injection of cells without a delivery mechanism in a non-localized fashion presents a scenario of the therapeutic bone marrow cells competing with other cells in a potentially hostile environment and diminishing the chances of therapeutic benefit. Using an angiocath allows the dura to stay intact, allowing the physician to slide the lumen above and below the incised dura over the damaged level to the extent of the damage. With this advantage, the cells can be adequately delivered in a controlled fashion, in a contained environment away from other competing cells, and allow the therapeutic progenitor cells to attach to the extensions of the damaged cord areas. Past studies report lumbar puncture as the preferred route of administration for cell therapy treatment following cervical and/or thoracic spinal cord injury. The described approach is viewed as a critical improvement based upon the observed treatment response.

In another embodiment of the technique is the novel use of a common surgical device, gel foam. GELFOAM Sterile Compressed Sponge is a medical device intended for application to bleeding surfaces for hemostasis. It is well established that cell therapies need delivery vehicles to facilitate attachment, survival and differentiation of cells in a controlled fashion. GELFOAM has been studied as a cell delivery vehicle for tissue regeneration applications, as well as, resorbable hydrogels in spinal cord injury and is considered safe. The remaining half of the concentrated volume is soaked to a piece of GELFOAM and placed on top of the sutured dura. Due to the GELFOAM resorbable and time release properties, it provides an ideal cell delivery vehicle for the remaining volume of concentrate over the sutured dura. Furthermore, although its mechanism of action is not well understood, it is believed to result in the local production of thrombin, initiating the clotting cascade. Thrombin converts fibrinogen to an insoluble fibrin clot and activates platelet bonding to fibrin. Fibrin is considered a natural scaffold and has been used in numerous studies for stem cell delivery. So, it is theoretically possible that as the synthetic GELFOAM degrades, it is being replaced by the natural scaffold fibrin. Furthermore, GELFOAM acts as a reservoir for timed release of growth factors and the genetic material delivered as part of the associated platelet and exosome fractions, respectively. Hydrogels have long been studied and used as cell delivery vehicles even in spinal cord injury studies and are considered safe. They provide a controlled time released delivery due to hydrogels resorption characteristics. However, hydrogels have not been used in combination with free stem cells for spinal cord injury. Furthermore, previous studies have utilized hydrogels prepared with embedded stem cells directly on the spinal cord. With this technique, cell therapy infused GELFOAM is placed on top of the sutured dura after the free stem cells have bathed the spinal cord. This calls upon many known tissue regeneration principles important for this specific treatment—time released delivery of cells superficially, granulation and rapid repair of the incised dura, and a protective layer over the incised/sutured dura.

The 30cc of platelet-plasma added under and over the muscle/fascia complex is believed to have healing properties as it contains growth factors, peptides, and other soluble factors that have an established therapeutic, hemostatic, anti-inflammatory, and infection control benefits which may also assist in the healing process. For example, Vascular endothelial growth factors and Bcl-xL levels have been shown to decrease after spinal cord injuries in rats and their decrease correlates well with apoptosis, suggesting they may play a role in neural sparring. Additional delivery of PDGF-AA and FGF-2 may provide trans differentiation factors resulting in induction of new oligodendrocytes from stromal precursors delivered as part of the cellular therapy. Furthermore, plasma is rich in anti-inflammatory proteins, exosomes, and other genes that would encourage tissue genesis and regeneration.

The "bathing" technique described utilizing large volumes of heterogenous stem cells could be utilized in any disease process of the spinal cord and brain to promote regeneration of tissue such as but not limited to: Multiple Sclerosis, Parkinson's Disease, degenerative diseases of the brain, transverse myelitis or congenital neurological abnormalities like myelomeningocele or even after tumor resection. If direct "bathing" by autologous stem cells (heterogeneous concentrate) is effective in the spinal cord, it may work when infused directly into the brain for example but not limited to the case of brain surgery for tumor resection. If "bathing" of the lesion by autologous stem cells is not feasible because surgery is not part of the treatment plan, an intrathecal administration via lumbar puncture using larger volumes of stem cells than have been used in the past, could be attempted.

Lastly, no studies to date have utilized MR guidance to determine the levels treated. Previous studies have focused on the bony injury as the gauge of localized spinal cord damage with some centering delivery at the level of bony injury extending delivery one level above and one below. MR imaging shows the extent of the SCI so that the affected levels can be treated effective. This technique utilized abnormal signal in the cord on T2WI on MRI as the guide for application.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method of treating a patient with a spinal cord injury, the steps consisting of:
   performing a posterior spinal fusion surgery, thereby exposing the injured spinal cord by opening skin, muscle, dura and arachnoid;
   applying a bone marrow concentrate under the dura and under the arachnoid to the injured spinal cord;
   bathing the exposed injured spinal cord and the surrounding with the bone marrow concentrate;
   suturing the dura to form dura sutures;
   applying the bone marrow concentrate to a sterile sponge; and
   applying the sterile sponge onto the dura and the dura sutures, followed by suturing the muscle and skin; and optionally a superficial plasma layer is also applied to the sutures.

2. The method of claim 1, wherein the posterior spinal fusion surgery and the applying of the bone marrow concentrate are guided by magnetic resonance imaging to determine the location and extent of the spinal cord injury.

3. The method of claim 2, wherein the bone marrow concentrate is derived from bone marrow aspirated from the patient and centrifuged into three layers comprising a red blood cell layer, the bone marrow concentrate, and a superficial plasma layer; wherein the bone marrow concentrate comprises a quantity of about 2 to 240cc.

4. The method of claim 3, wherein the superficial plasma layer is applied to the dura sutures and the sterile sponge.

5. The method of claim 4, wherein the muscle is sutured and the superficial plasma layer is applied to the sutured muscle.

6. The method of claim 2, wherein the bone marrow concentrate is slowly injected under the dura and under the arachnoid to the injured spinal cord and then the exposed injured spinal cord and the surrounding are bathed with the bone marrow concentrate with a flexible tip angiocath.

7. The method of claim 6, wherein the injecting is repeated to all cord levels showing injury, wherein the injecting is done sequentially, and wherein about 0.5 to 1.0 ml of bone marrow concentrate is injected for about every 1 cm of insertion.

8. The method of claim 7, wherein the sterile sponge comprises a water insoluble, off-white, non-elastic, porous, pliable product prepared from purified pork skin gelatin granules and water.

9. A method of treating a patient with a spinal cord injury, the steps consisting of:
- performing a posterior spinal fusion surgery, thereby exposing the injured spinal cord by opening skin, muscle, dura and arachnoid;
- applying a bone marrow concentrate under the dura and under the arachnoid to the injured spinal cord;
- bathing the exposed injured spinal cord and the surrounding with the bone marrow concentrate;
- suturing the dura to form dura sutures;
- applying the bone marrow concentrate to a sterile sponge;
- applying the sterile sponge onto the dura and the dura sutures, followed by suturing the muscle and skin;
- wherein the posterior spinal fusion surgery and the applying of the bone marrow concentrate are guided by magnetic resonance imaging to determine the location and extent of the spinal cord injury; and
- wherein the bone marrow concentrate is derived from bone marrow aspirated from the patient and centrifuged into three layers comprising a red blood cell layer, the bone marrow concentrate, and a superficial plasma layer; and optionally the superficial plasma layer is also applied to the sutures.

10. The method of claim 9, wherein the superficial plasma layer is applied to the dura sutures and the sterile sponge.

11. The method of claim 10, wherein the muscle is sutured and the superficial plasma layer is applied to the sutured muscle.

12. The method of claim 11, wherein the bone marrow concentrate is slowly injected under the dura and under the arachnoid to the injured spinal cord and then the exposed injured spinal cord and the surrounding are bathed with the bone marrow concentrate with a flexible tip angiocath.

13. The method of claim 12, wherein the injecting is repeated to all cord levels showing injury, wherein the injecting is done sequentially, and wherein about 0.5 to 1.0 ml of bone marrow concentrate is injected for about every 1 cm of insertion.

* * * * *